United States Patent

Avida et al.

[11] Patent Number: 5,235,182
[45] Date of Patent: Aug. 10, 1993

[54] SPECTROMETER

[75] Inventors: Ram Avida; Menahem Friedman, both of Omer; Asaf Algom, Metar; Avner Matmor; Zeev Karpas, both of Omer; Oded Shahal, Beer-Sheva, all of Israel

[73] Assignee: State of Israel, Atomic Energy Commission Research Center Negev, Beer-Sheva, Israel

[21] Appl. No.: 856,582

[22] Filed: Mar. 24, 1992

[30] Foreign Application Priority Data

Apr. 1, 1991 [IL] Israel .................................. 97742

[51] Int. Cl.$^5$ ............................................. H01J 49/40
[52] U.S. Cl. .................................. 250/286; 250/287
[58] Field of Search ............... 250/286, 287, 281, 282

[56] References Cited

U.S. PATENT DOCUMENTS

| | | | |
|---|---|---|---|
| 4,238,678 | 12/1980 | Castelman et al. | 250/287 |
| 4,378,499 | 3/1983 | Spangler et al. | 250/287 |
| 4,390,784 | 6/1983 | Browning et al. | 250/286 |
| 4,551,624 | 11/1985 | Spangler et al. | 250/287 |
| 4,633,083 | 12/1986 | Knorr et al. | 250/287 |
| 4,777,363 | 10/1988 | Eiceman et al. | 250/287 |
| 4,839,143 | 6/1989 | Vora et al. | 250/286 |

*Primary Examiner*—Paul M. Dzierzynski
*Assistant Examiner*—Kiet T. Nguyen
*Attorney, Agent, or Firm*—Merchant & Gould, Smith, Edell, Welter & Schmidt

[57] ABSTRACT

In an ion mobility spectrometer comprising a spectrometer tube with an ion shutter, an ionization source within a reaction chamber, and a drift chamber, the improvement comprises providing in or around the said drift tube a plurality of conducting segments, across which an electric field is applied, the said conducting segments being separated from one another by insulating spacers, wherein the ratio between the width of the insulating spacers to the width of the conducting segments is between 2:1 and 1:1, preferably about 1.5:1.

7 Claims, 4 Drawing Sheets

SPECTROMETER

FIELD OF THE INVENTION

The present invention relates to a spectrometer. More particularly, the invention relates to an improvement in the construction of ion mobility spectrometers.

BACKGROUND OF THE INVENTION

Ion mobility spectrometers (IMS) consist of an ionizer coupled via a shutter grid to an ion drift region. Gas or vapor to be analyzed is introduced into a reactor or ionizer by means of a carrier gas. In the reactor, the carrier molecules are ionized, normally by $\beta$ irradiation from an Ni-63 radioactive source. Reactant ions are produced from the carrier gas and product ions are produced from reaction of reactant ions with the sample. Under the influence of an applied electric field, the reactant and product ions are extracted from the plasma generated near the radioactive source and are drawn to a shutter grid where they are pulsed as finite slugs of ions into the ion drift region. The ion drift region is a cylindrical cavity around which coaxial guard rings are positioned, and at the end of which a collector is positioned, to intercept and count the ions that reach it. The motion of the ion population, during the time between its entrance into the drift region and its arrival at the collector, is determined by the electric field applied across the guard rings, the temperature and pressure within the spectrometer and the nature of the ions. Spectrometers of this type are well known in the art and are described, e.g., in GB 2217103, and in U.S. Pat. No. 4,777,363. The sensitivity of this type of spectrometer is limited by two factors. Firstly, the number of ions which are generated in the reaction zone is relatively low, and only a small percentage of them pass through the shutter grid, so that the pulse of ions reaching the drift region is low. Secondly, the trajectory of the ions entering the drift region at the shutter, until they reach the collector is influenced by the electric field generated by the coaxial guard rings. Because this trajectory is not straight, some of the ions which enter the drift region at the shutter do not reach the collector, thus reducing the ion current intensity of the reading of the spectrometer. Given the limitation of the radioactive source, which generates a finite number of ions, control over the trajectory of the ions should be gained, in order to increase this reading.

Furthermore, the spread in the drift times of ions of the same type, travelling from grid to collector, is indicative of the tube resolution. The narrower the spread the higher the resolution and the ability accurately to determine the mobility and to establish the identity of the ions.

Several attempts have been made to obtain a homogeneous electric field within the drift tube or region, mainly by increasing the size of the metallic rings, and reducing the size of spacer or insulating rings. Typically, IMS devices known in the art have ratios of about 1:10 between the width of the insulating ring to the width of the conductive metallic rings.

SUMMARY OF THE INVENTION

It has now been most surprisingly found, and this is an object of the present invention, that in order to minimize the drift time-spread and to maximize the number of ions reaching the collector after entering the drift region at the shutter, it is necessary to provide a slightly focusing electric field, and not a homogeneous electric field. The required slightly focusing electric field is obtained by providing a ratio between the width of the insulating and metallic segments quite different from those customary in the art. In fact, the width of the insulating segments should be greater than the width of each metallic segment. The word "segment" herein is intended to indicate all possible shapes, such as rings, square shapes with internal ring-shape, etc., and any appropriate shape of the insulating and conducting segments will be possible, as will be apparent to a skilled person.

Thus, the improvement provided by the present invention consists of providing in or around the drift tube, a plurality of segments made of conductive material, e.g. metallic segments, such as rings,, separated from one another by insulating segments, wherein the ratio between the width of the insulating segment to the width of the conducting segment is between 2:1 and 1:1. It has been found that a preferred ratio is about 1.5:1. The improvement according to the invention is not limited to the use in any specific IMS device, and may be employed in a variety of devices. For instance, if the device employs an atmospheric or almost atmospheric pressure, then the drift tube may be built of interconnected spacer and metallic segments. If high pressure or highly corrosive materials are involved, on the other hand, the drift tube may be, e.g., a glass tube, and metallic segments of the appropriate dimensions can be provided around the glass tube at the correct openings. Alternatively, the drift tube can be made of - or coated with - corrosion-resistant material.

In a preferred embodiment of the invention all conducting segments have substantially the same width, and also all the insulating segments have substantially the same width, which, of course, is different from the width of the conducting segments. According to a preferred embodiment of the invention, the insulating segments are ring-shaped and are made of Teflon and the distance between adjacent segments would preferably be equal to or up to twice the width of the conducting segments, but of course any other suitable insulating material can be employed.

BRIEF DESCRIPTION OF THE DRAWINGS

To further illustrate the invention, a preferred embodiment will now be described with reference to the appended drawings, wherein.

DETAILED DESCRIPTION OF PREFERRED EMBODIMENTS

Figure 1:
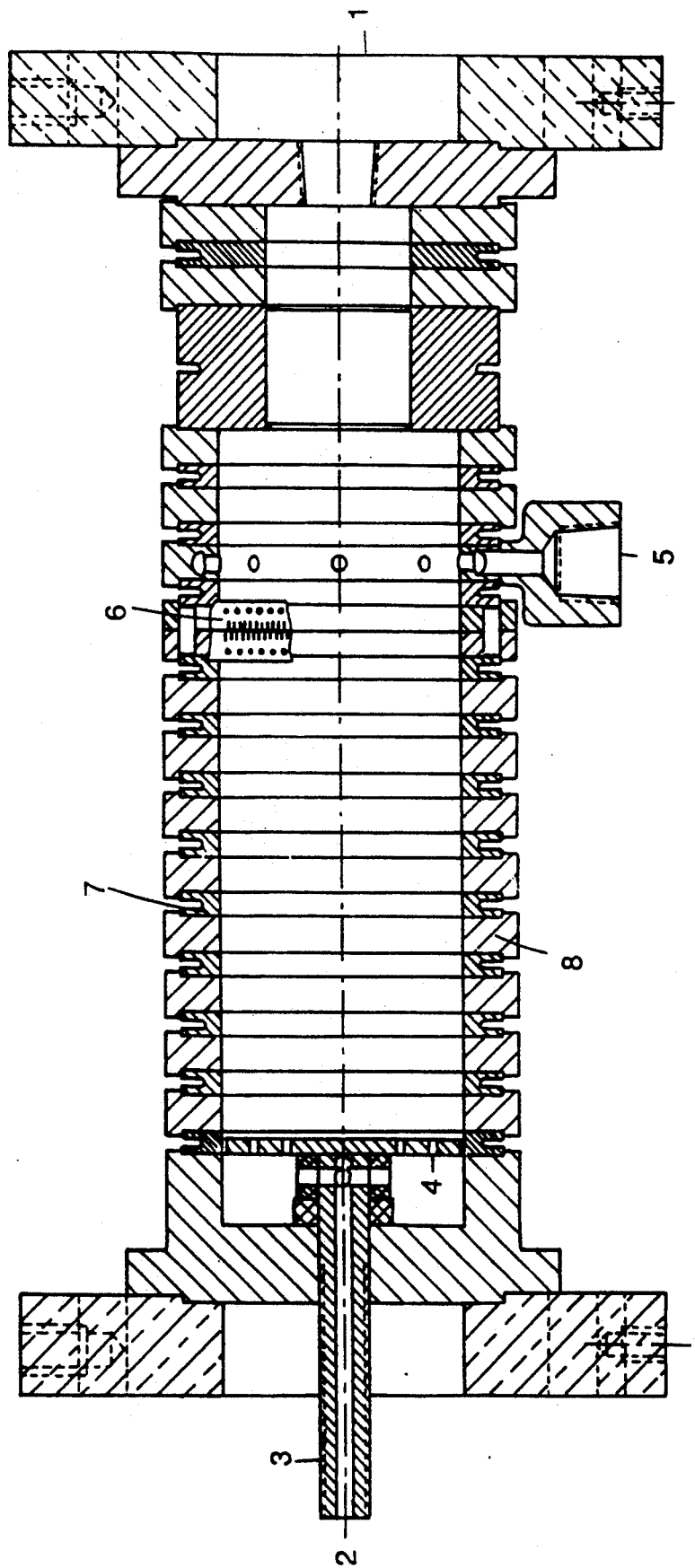
FIG. 1 is a cross-section of a device according to an embodiment of the invention.

With reference now to FIG. 1, the carrier and sample enter the IMS device through inlet 1, while the drift gas enters through inlet 2. The drift gas, which enters through hollow shaft 3, is distributed into the drift zone through holes 4. All gases leave the IMS through exit 5. The shutter is shown in partial cross-section and is indicated by numeral 6.

As can be seen from the figure, metallic rings 7 are separated by insulating rings 8, which are of greater width than metallic rings 7. These metallic rings 7, in turn, are connected to appropriate voltage generating means, not shown in the figure for the sake of simplicity.

Figure 2:
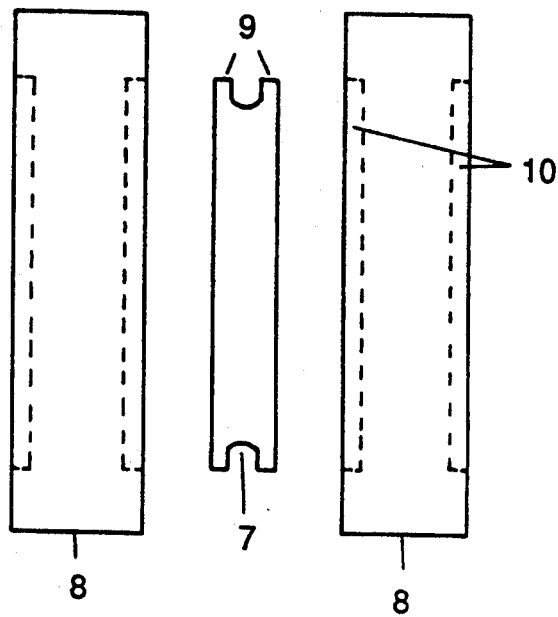
FIG. 2 shows the connection between two adjacent rings.

Turning now to FIG. 2, two ring elements, one ring element 7 and one ring element 8 are seen, which fit into a charter when the male portion 9 of the metallic ring 7 fits into the recessed portion 10 of the insulating ring 8. Ring 7 has two such male portions 9, to fit into an insulating ring on each side, and each insulating ring 8 is provided with two matching recessed portions 10.

Figure 3:
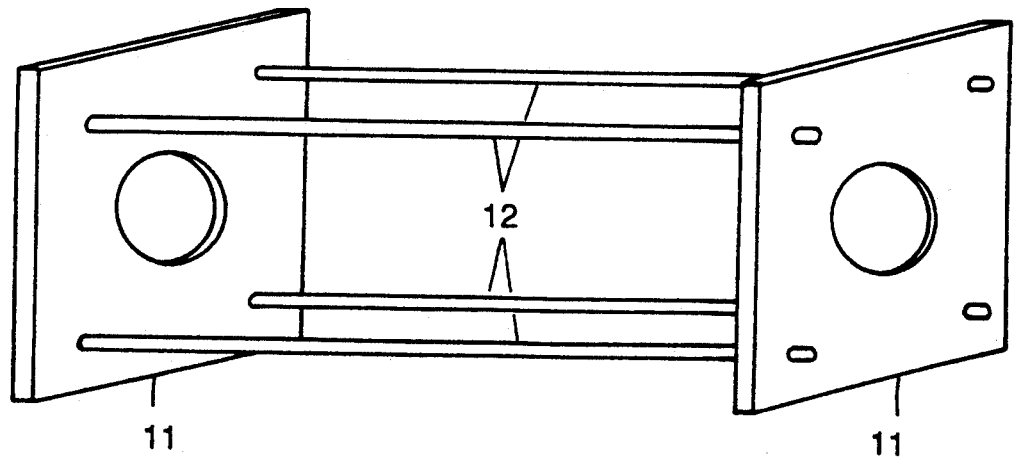
FIG. 3 illustrates the terminal elements and tension means to be used together with the rings of FIG. 2.
Figure 4A:
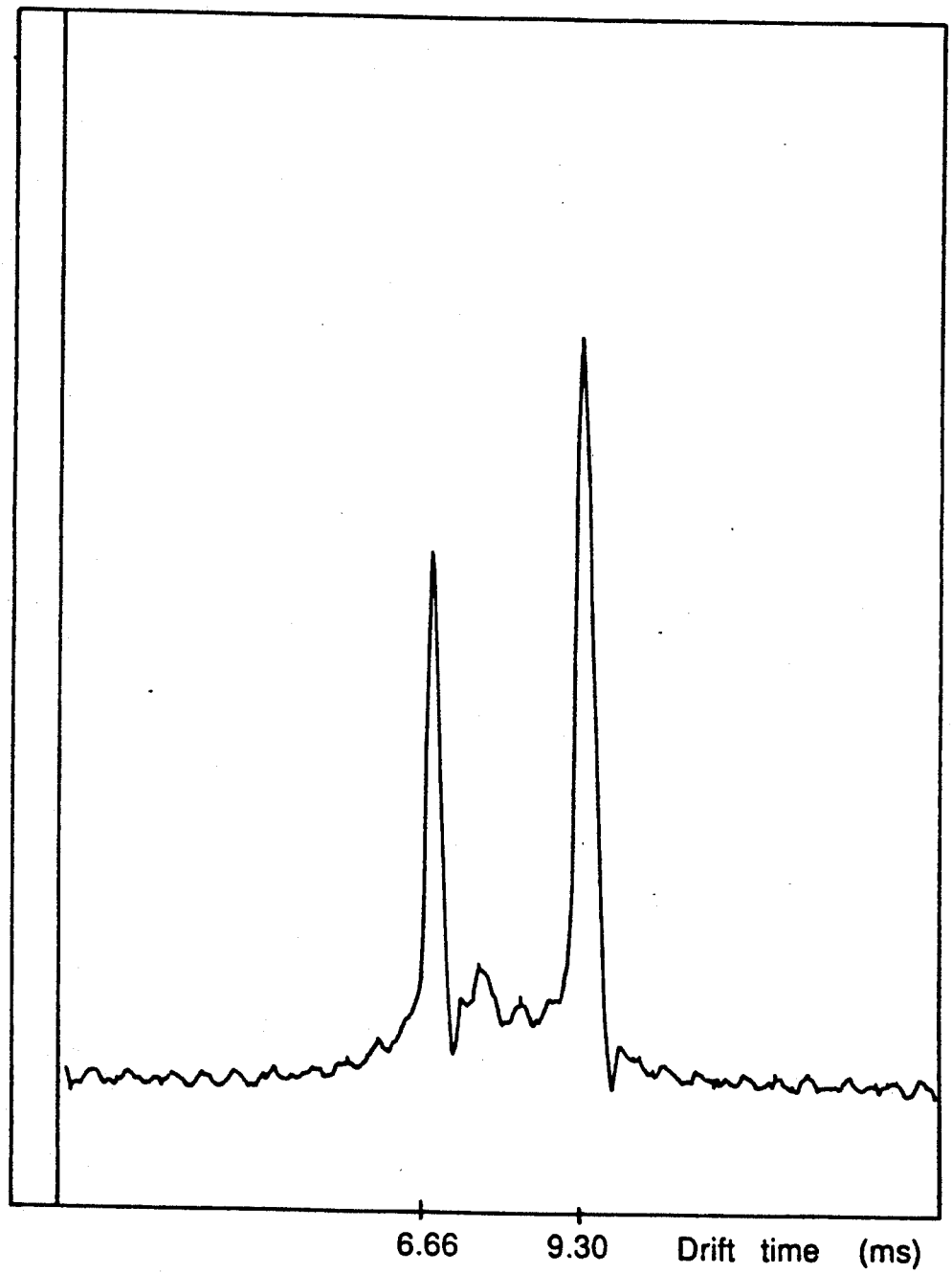
FIGS. 4(*a–b*) illustrate the performance of a device according to e preferred embodiment of the invention.
Figure 4B:
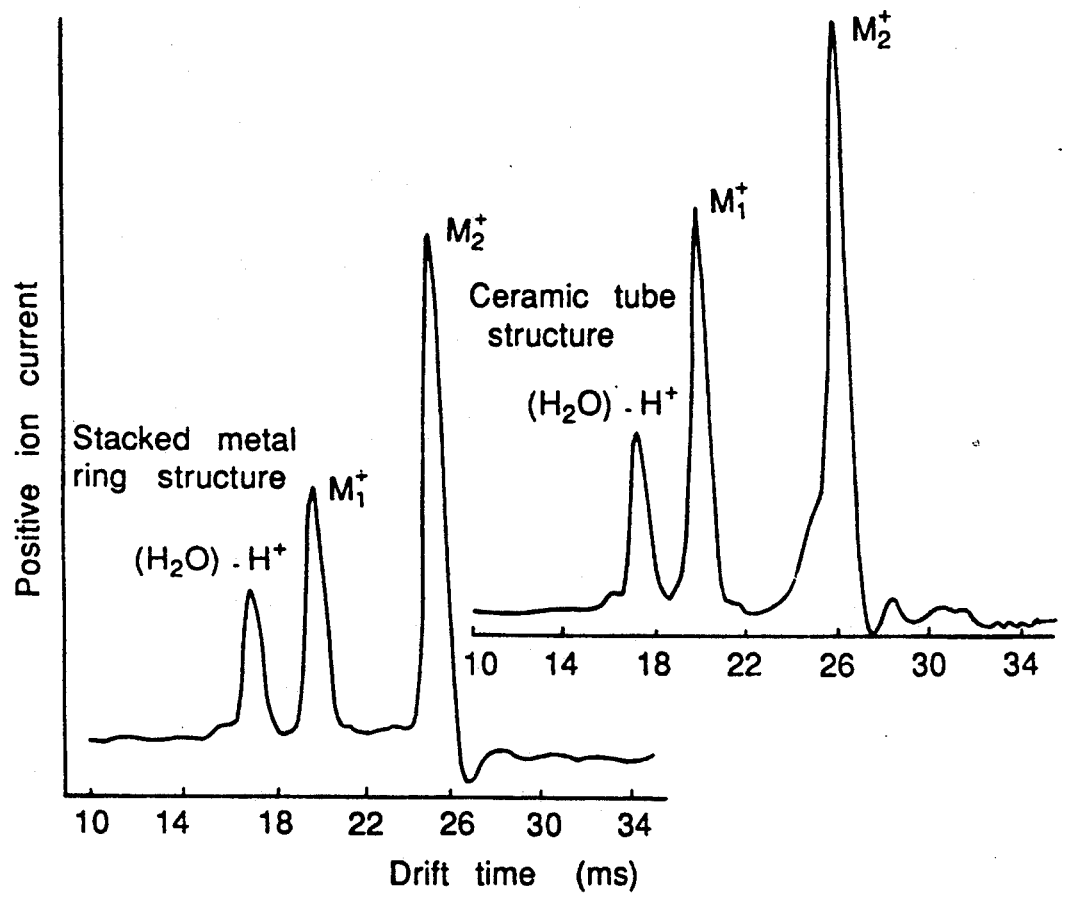

In FIG. 3 two end elements 11 are shown, which will hold the drift tube, made of intercalated rings 7 and 8, by means of tension rods 12, which will apply a tension on the assembled tube, and to the intercalated rings 7 and 8 between the two end elements 11 (not shown in the figure), and will thus keep the tube in place. FIG. 4 illustrates the performance of a device according to a preferred embodiment of the invention. This figure shows the spectra of dimethylmethylphosphonate obtained with a device according to the invention (FIG. 4(a)), and with prior art devices (FIG. 4(b)), as described by Carrico et al. [J. Phys. E:Sci. Instrum., Vol. 16, 1983, pp. 1058-62].

The prior art devices employed have the characteristics listed in Table 1 (page 1059) of the Carrico et al. article, viz. drift lengths of 76 mm and 93 mm respectively. The device according to the invention, in contrast, had a drift length of 57.6 mm. The drift region of the device was equipped with 8 metallic rings having a thickness of 2.8 mm, and with 8 intervening insulating spacers having a thickness of 4.4 mm. As can be seen by comparing the spectra of FIG. 4, the device of the invention provides a performance essentially identical to that of the prior art devices, although its dimensions are substantially smaller.

The spectrum of FIG. 4(a) was obtained using an experimental procedure as discussed in the Carrico et al. article. The drift cell temperature was 175° C., the drift voltage was 2900 V, the atmospheric temperature was 720 torr and the gate width of the shutter grid pulse was 0.1 msec.

Thus, as will be apparent to a person skilled in the art, the device according to the leads to surprising results, while maintaining small and compact dimensions. Of course, many modifications and embodiments can be provided, on the basis of the invention, which will be apparent to the skilled person, and which will not depart from the scope of the invention.

We claim:

1. In an ion mobility spectrometer comprising a spectrometer tube with an ion shutter, an ionization source within a reaction chamber, and a drift chamber, the improvement consisting of providing in or around the said drift tube a plurality of conducting segments, across which an electric field is applied, the said conducting segments being separated from one another by insulating spacers, wherein the ratio between the width of the insulating spacers to the width of the conducting segments is between 2:1 and 1:1, preferably about 1.5:1.

2. A spectrometer according to claim 1, wherein all conducting segments have substantially the same width.

3. A spectrometer according to claim 1, wherein all insulating spacers have substantially the same width.

4. A spectrometer according to claim 3, wherein the insulating spacers are made of Teflon.

5. A spectrometer according to claim 3, wherein the conducting segments and the insulating spacers fit into one another in a male to female connection, and are held in place by tension means coupled to end elements.

6. A spectrometer according to claim 5, wherein the conducting segments are metallic segments, such as metallic rings.

7. A spectrometer according to claim 6, wherein the distance between two adjacent conducting segments is equal to or up to twice the width of the conducting segments.

* * * * *